US008618188B2

(12) United States Patent
Gruskin et al.

(10) Patent No.: US 8,618,188 B2
(45) Date of Patent: Dec. 31, 2013

(54) BONE CEMENT WITH ADAPTED MECHANICAL PROPERTIES

(75) Inventors: Elliott Gruskin, Malvern, PA (US); Andreas Boger, Rheinfelden (CH); Andrea Montali, Basel (CH); Kurtis Wheeler, Biberist (CH)

(73) Assignee: DePuy Synthes Products, LLC, Raynham, MA (US)

( * ) Notice: Subject to any disclaimer, the term of this patent is extended or adjusted under 35 U.S.C. 154(b) by 433 days.

(21) Appl. No.: 12/529,562

(22) PCT Filed: Feb. 29, 2008

(86) PCT No.: PCT/US2008/002811
§ 371 (c)(1),
(2), (4) Date: Sep. 2, 2009

(87) PCT Pub. No.: WO2008/109045
PCT Pub. Date: Sep. 12, 2008

(65) Prior Publication Data
US 2010/0056654 A1    Mar. 4, 2010

Related U.S. Application Data

(60) Provisional application No. 60/904,673, filed on Mar. 2, 2007, provisional application No. 60/967,052, filed on Aug. 31, 2007.

(51) Int. Cl.
*A61F 2/28* (2006.01)
*A61F 2/00* (2006.01)
*C08F 120/14* (2006.01)

(52) U.S. Cl.
USPC ........... 523/116; 523/115; 523/117; 523/118; 424/423; 525/311; 521/50

(58) Field of Classification Search
USPC .................... 521/50; 523/116, 117, 118, 115; 424/423
See application file for complete search history.

(56) References Cited

U.S. PATENT DOCUMENTS

| 4,093,576 A | 6/1978 | deWijn | |
|---|---|---|---|
| 5,797,873 A * | 8/1998 | Franz et al. | 604/500 |
| 7,651,701 B2 * | 1/2010 | Meyer et al. | 424/487 |
| 2006/0041033 A1 * | 2/2006 | Bisig et al. | 523/116 |

FOREIGN PATENT DOCUMENTS

| DE | 19641775 A1 | 2/1998 |
|---|---|---|
| EP | 0111759 A2 | 6/1984 |
| EP | 0701824 A2 | 3/1996 |
| WO | WO-2004071543 A1 | 8/2004 |

OTHER PUBLICATIONS

"International Application Serial No. PCT/US2008/002811, Search Report mailed May 28, 2009", 7 pgs.

(Continued)

*Primary Examiner* — Randy Gulakowski
*Assistant Examiner* — Kara Boyle
(74) *Attorney, Agent, or Firm* — Woodcock Washburn LLP

(57) ABSTRACT

A bone cement is shown that includes a monomer, and a non-reactive substance that is fully miscible with the monomer. A resulting cured bone cement exhibits desirable properties such as modification in a stiffness of the material. Modified properties such a stiffness can be tailored to match bone properties and reduce an occurrence of fractures adjacent to a region repaired with bone cement. One example includes adjacent vertebral body fractures in vertebroplasty procedures.

15 Claims, 1 Drawing Sheet

(56) References Cited

OTHER PUBLICATIONS

"International Application Serial No. PCT/US2008/002811, Written Opinion mailed May 28, 2009", 8 pgs.

Bruens, M. L, et al., "Porous Polymethylmethacrylate As Bone Substitute in The Craniofacial Surgery Burlington", Vo.14, No. 1, ISSN, (Jan. 1, 2003), 63-68 pgs.

* cited by examiner

BONE CEMENT WITH ADAPTED MECHANICAL PROPERTIES

RELATED APPLICATION

This patent application is a U.S. National Stage Filing under 35 U.S.C. 371 from International Patent Application Serial No. PCT/US2008/002811 filed Feb. 29, 2008, and published on Sep. 12, 2008, as WO 2008/109045 A2 and republished as WO 2008/109045 A3, which claims the priority benefit of U.S. Provisional Patent Application Ser. No. 60/904,673 filed Mar. 2, 2007 and entitled "PMMA CEMENT WITH ADAPTED MECHANICAL PROPERTIES" and to U.S. Provisional Patent Application Ser. No. 60/967,052 filed Aug. 31, 2007 and entitled "PMMA CEMENT WITH ADAPTED MECHANICAL PROPERTIES", the contents of which are incorporated herein by reference in their entirety.

BACKGROUND

Vertebral compression fractures in osteoporotic patients are typically treated by a surgical procedure known as vertebroplasty. In this procedure the fractured vertebral body is augmented with a bone cement. The bone cement polymerizes and hardens upon injection into the vertebral body and stabilizes the fracture. Pain relief for the patient is usually immediate and vertebroplasty procedures are characterized by a high rate of success.

Typically, bone cement is prepared directly prior to injection by mixing bone-cement powder (e.g., poly-methyl-methacrylate (PMMA)), a liquid monomer (e.g., methyl-methacrylate monomer (MMA)), an x-ray contrast agent (e.g., barium sulfate), and an activator of the polymerization reaction (e.g., N, N-dimethyl-p-toluidine) to form a fluid mixture. Other additives including but not limited to stabilizers, drugs, fillers, dyes and fibers may also be included in the bone cement. Since the components react upon mixing, immediately leading to the polymerization, the components of bone cement must be kept separate from each other until the user is ready to form the desired bone cement. Once mixed, the user must work very quickly because the bone cement sets and hardens rapidly.

Other examples of bone cement compositions and/or their uses are discussed in U.S. Pat. No. 7,138,442; U.S. Pat. No. 7,160,932; U.S. Pat. No. 7,014,633; U.S. Pat. No. 6,752,863; U.S. Pat. No. 6,020,396; U.S. Pat. No. 5,902,839; U.S. Pat. No. 4,910,259; U.S. Pat. No. 5,276,070; U.S. Pat. No. 5,795,922; U.S. Pat. No. 5,650,108; U.S. Pat. No. 6,984,063; U.S. Pat. No. 4,588,583; U.S. Pat. No. 4,902,728; U.S. Pat. No. 5,797,873; U.S. Pat. No. 6,160,033; and EP 0 701 824, the disclosures of which are herein incorporated by reference.

The elastic moduli of typical PMMA bone cements lie around 2-4 GPa, while the elastic modulus of osteoporotic cancellous bone lies in the range of 0.1-0.5 GPa. This mismatch in stiffness is generally perceived as favoring the subsequent fracturing of the vertebral bodies that are adjacent to the augmented vertebral body.

It is therefore an object of the invention to obtain a bone cement with a reduced stiffness that is adapted to the stiffness of the surrounding bone. This is thought to be an efficient way to reduce the risk of adjacent vertebral body fractures after the augmentation of vertebral bodies.

Reduction of the stiffness by introducing non-miscible phases, such as aqueous components, into the PMMA upon polymerization is well known and has been described before. This leads to a macroporous structure with reduced stiffness.

SUMMARY OF THE INVENTION

The invention relates to a bone cement including a monomer and a substance that is substantially miscible with the monomer and substantially does not contribute to a polymerization reaction. In one embodiment of the invention, the substance is N-methyl-pyrrolidone. In another embodiment, the substance is dimethyl-sulfoxide (DMSO). In another embodiment, the substance is polyethylene glycolide (PEG). In another embodiment, the substance is cellulose and cellulose derivates. In another embodiment, the substance is a mixture or blend of the mentioned substances or other, comparable substances. In another embodiment, the substance reduces a crosslink density of the bone cement. In another embodiment, the substance creates a microporous structure in the bone cement. In another embodiment, the bone cement further includes polymerization of the monomer. In another embodiment, a portion of the monomer in substituted by the substance during polymerization. In another embodiment, substitution of the monomer by the substance yields a decrease in the stiffness of the bone cement.

The invention also relates to a bone cement including methyl-methacrylate and N-methyl-pyrrolidone. In one embodiment of the invention the volume percentage of the methyl-methacrylate which is substituted by NMP, DMSO, PEG or other analogous substances lies in the range of 20%-60%. One specific example includes a volume percentage substitution of 25%. The volume of MMA can be substituted by either one of the pure substances mentioned above or by a mixture of these substances. In another embodiment of the invention, a stiffness of the bone cement is between about 100 MPa to about 2000 MPa. In another embodiment of the invention, a stiffness of the bone cement is between about 100 MPa to about 1500 MPa. In another embodiment of the invention, a stiffness of the bone cement is between about 500 MPa to about 1200 MPa. In another embodiment of the invention, a yield strength of the bone cement is from about 30 MPa to about 100 MPa. In another embodiment of the invention, a yield strength of the bone cement is from about 30 MPa to about 80 MPa.

DETAILED DESCRIPTION

Figure 1:
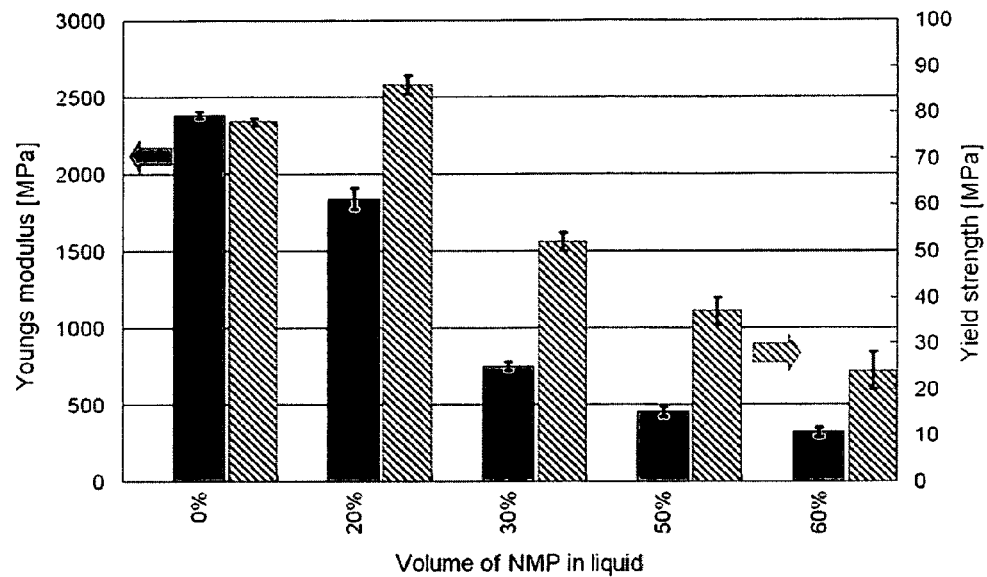
FIG. 1 is a graph showing the stiffness and yield strength of bone cements according to an embodiment of the present invention.

The present invention relates to a polymer bone cement or a derivative thereof having improved mechanical properties that is adapted to bone or osteoporotic bone. In one embodiment of the invention, the polymer bone cement is PMMA. The improved mechanical properties are achieved by adding a fully miscible solvent that does not react with the PMMA to the reactive MMA monomer. By doing so, the crosslink density of the material and the stiffness can be reduced.

The present invention is based on using a substance that is fully miscible with the monomer and is, therefore, molecularly dissolved in the PMMA after polymerization. However, due to its non-reactivity, this leads to a reduction in the final crosslink density and/or to a material with a microporous structure and, therefore, the stiffness of the material is reduced. After implantation and full polymerization of the material, the crosslink-lowering substance may be gradually substituted by body fluids.

This concept was tested by substituting different amounts of the reactive monomer with N-methyl-pyrrolidone (NMP), which does not contribute to the polymerization reaction. Subsequent mechanical testing of PMMA samples produced in this way showed a reduction in stiffness greater than about 50% in some embodiments.

The described effect of lowering the stiffness of the material can be obtained with any solvent that is miscible with the monomer of PMMA but does not contribute to the polymerization reaction. Another example of such of a solvent is Dimethyl-sulfoxide (DMSO). In other embodiments, a range of other solvents can also be envisioned. In another embodiment, substances such as PEG, cellulose, cellulose derivates or mixtures thereof can be added.

Furthermore, the present concept is not limited to PMMA cements, it can be applied to a wide variety of derivatives of PMMA, e.g. modifications in which Styrene groups are built into the polymer backbone. The same concept also applies to cements that are not based on the acrylate chemistry.

A material as described above, with mechanical properties adapted to those of e.g. osteoporotic bone can be used in any indication, where bone needs to be augmented, e.g. the proximal femur, the proximal humerus, long bones, vertebral bodies or the like.

As shown by the data in Table 1, the bone cements according to embodiments of the present invention that include NMP exhibit a decrease in stiffness when compared to the bone cement without NMP. The decrease in stiffness occurs as a result of the substitution of some of MMA monomer by NMP. According to some embodiments, by substituting a part of the reactive liquid MMA monomer with non-reactive organic solvent NMP during polymerization, the crosslink density in the final material was lowered and therefore the stiffness of the material was reduced. In other embodiments, the NMP can act as a pore forming phase, resulting in bone cement having a microporous structure. As discussed above, a decrease in stiffness is an efficient way to reduce the risk of adjacent vertebral body fractures in vertebroplasty procedures.

In some embodiments, the bone cements including NMP demonstrate an increase in hardening time. That is, the time for the bone cement to set and harden is longer for the cements having an NMP component. In some embodiments, an increase in handling time allows for greater working time for the user, which can increase the safety of surgical procedures.

In addition to the reduced stiffness, another property which is influenced by the mentioned modification is the maximum polymerization temperature of the exothermic polymerization of PMMA. Typically, polymerization of the PMMA can generate enough heat and increase the temperature of the bone cement to such a degree as to cause tissue necrosis. Because the bone cements of the present invention includes a lower content of monomer (MMA), which is the component that generates the heat during the polymerization reaction, the maximum polymerization temperature can be lowered. This is particularly advantageous because tissue necrosis may be reduced or avoided when the bone cement of the present invention is used, which allows for the use of the bone cement in areas of the body which are particularly sensitive to heat. For example, bone necrosis or other tissue necrosis can be a substantial problem during cranial reconstruction where the bone cement may contact the dura mater, due to the delicacy of the tissues and bone structures. Use of a bone cement having reduced heat generation is therefore particularly desirable in these areas.

Another advantage of the bone cements of the present invention is the potential reduction in the toxicity of the composition. Bone cement monomers, including methyl methacrylate, give off toxic vapors which can be irritating to the eyes and respiratory system. Furthermore, acrylate monomers can irritate the skin, and contact with minute concentrations can cause sensitization. Therefore, since the bone cement of the present invention uses a lower amount of monomer, the potential for the above problems to occur while using the bone cement of the present invention may be reduced.

In some embodiments of the present invention, the bone cement can be useful for vertebroplasty. The mentioned properties of hardening behavior, mechanical and thermal properties especially increasing of the handling time (more time for the surgeon and therefore more safety), lowering the stiffness (avoiding the mechanical property mismatch of the bone to the cement) and reducing the polymerization temperature (reduce tissue necrosis) are important properties for cement used in vertebroplasty. It is possible, that all of these requirements could be achieved by substituting some of the MMA monomer with NMP.

Example

The following example was carried out using commercial PMMA cement Vertecem. Vertecem is a fast setting, radiopaque acrylic bone cement for use in percutaneous vertebroplasty. The fluid phase is composed of 97.6% methyl-methacrylate (MMA), 2.4% N, N-dimethyl-p-toluidine as activator and very small quantities (20 ppm) of hydroquinones as stabilizer. The polymer powder is composed of 64.4% PMMA, 0.6% benzoyl peroxide which initiates the polymerization, 25% barium sulfate as radiopaque agent and 10% hydroxyapatite.

The fluid MMA monomer phase was partly substituted by NMP organic solvent by different amounts. NMP is totally miscible with the MMA monomer fluid. The amounts of MMA, and NMP, and PMMA used in the different compositions are listed in Table 1.

TABLE 1

| Sample Name | MMA/ ml | NMP/ ml | PMMA Powder/g | Stiffness/ MPa Average | Yield Strength/ MPa Average |
| --- | --- | --- | --- | --- | --- |
| 0% | 10 | 0 | 21 | 2384 | 78 |
| 20% | 8 | 2 | 21 | 1838 | 86 |
| 30% | 7 | 3 | 21 | 752 | 52 |
| 50% | 5 | 5 | 21 | 456 | 37 |
| 60% | 4 | 6 | 21 | 320 | 24 |

The MMA monomer and NMP was premixed to form a fluid mixture. Subsequently the fluid mixture was mixed with the PMMA powder to form a paste. To prepare the samples for mechanical testing, the paste was filled into cylindrical Teflon® molds (20 mm height, 6 mm diameter). The hardened cylinders were then removed from the mold, sawed and ground to the length of 12 mm, these dimensions correspond to the requirements of standard ISO 5833. After storing the samples in water for 6 days at room temperature they were submitted for mechanical compression testing according to standard ISO 5833. The elastic modulus and yield strength were determined according to the mentioned standard and presented in FIG. 1. Results are shown in FIG. 1, illustrating trends versus percent of MMA that is substituted by NMP.

Figure 2:
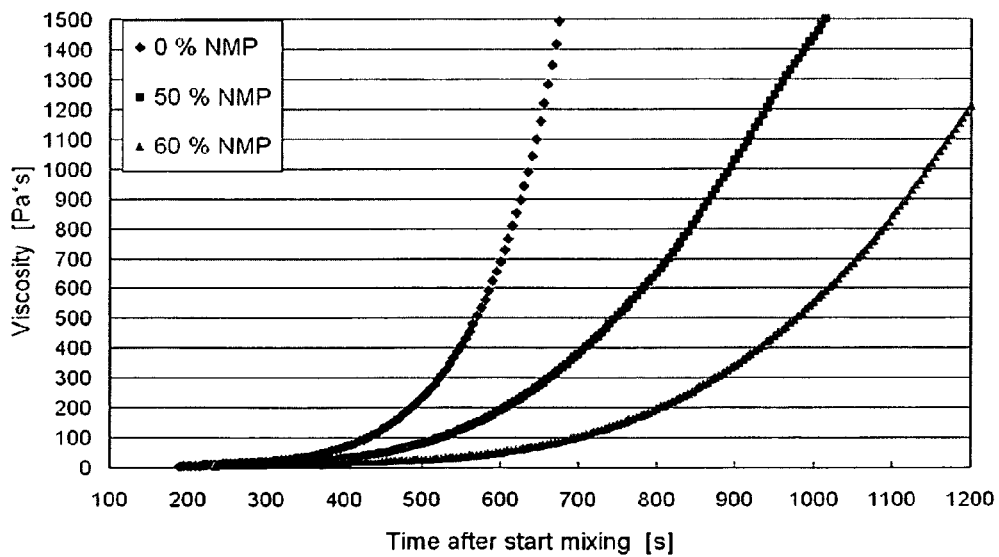
FIG. 2 is a graph showing the hardening behavior of bone cements in accordance with an embodiment of the present invention.

For the investigation of the hardening behavior of the cement compositions, 3 ml of the mixed bone cement were placed in a rotational rheometer with a custom designed double gap measurement system and rheological data were recorded directly to a computer for 24 portions of cement. The real (fluid-like) part of complex viscosity vs. time data are presented in FIG. 2.

What is claimed is:

1. A bone cement formed from a mixture of a fluid phase and a powder phase, the mixture consisting of:
   (i) a powder phase having poly methyl(meth)acrylate or derivatives thereof, an initiator compound, a radiopaque agent, and optionally, hydroxyapatite; and,
   (ii) a fluid phase having a reactive monomer, an activator, a stabilizer, and, a substance that is N-methyl-pyrrolidone (NMP), dimethyl-sulfoxide (DMSO), polyethylene glycolide (PEG), cellulose, cellulose derivates, or mixtures thereof;
   wherein the substance comprises an amount between 30% and 60% of the fluid phase.

2. The bone cement according to claim 1, wherein the substance is N-methyl-pyrrolidone.

3. The bone cement according to claim 1, wherein the substance is dimethyl-sulfoxide (DMSO).

4. The bone cement according to claim 1, wherein the substance is polyethylene glycolide (PEG).

5. The bone cement according to claim 1, wherein the substance is cellulose or cellulose derivate.

6. The bone cement according to claim 1, wherein the substance is a mixture of two or more of N-methyl-pyrrolidone, dimethyl-sulfoxide (DMSO), polyethylene glycolide (PEG), cellulose, or cellulose derivate.

7. The bone cement according to claim 1, wherein the substance creates a microporous structure in the bone cement.

8. The bone cement according to claim 1, wherein an elastic modulus of the bone cement is between 50 MPa and 2000 MPa.

9. The bone cement according to claim 1, wherein an elastic modulus of the bone cement is between 300 MPa and 1500 MPa.

10. The bone cement according to claim 1, wherein an elastic modulus of the bone cement is between 500 MPa and 1200 MPa.

11. The bone cement according to claim 1, wherein an elastic modulus of the bone cement is between 100 MPa and 1000 MPa.

12. The bone cement according to claim 1, wherein a yield strength of the bone cement is between 30 MPa and 100 MPa.

13. The bone cement according to claim 1, wherein a yield strength of the bone cement is between 40 MPa and 80 MPa.

14. The bone cement according to claim 1, wherein the bone cement, as hardened, has a Young's modulus that matches osteoporotic bone.

15. The bone cement according to claim 1, wherein the substance comprises an amount between 30% and 50% of the fluid phase.

* * * * *